(12) United States Patent
Fermier et al.

(10) Patent No.: US 6,674,022 B2
(45) Date of Patent: Jan. 6, 2004

(54) APPARATUS AND METHOD FOR TRANSFERRING AND WEIGHING POWDER MATERIALS USING PIPETTE TRANSFER DEVICES

(75) Inventors: Adam M. Fermier, Easton, PA (US); John Troisi, Neshanic Station, NJ (US); James V. Weber, Newtown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 28 days.

(21) Appl. No.: 09/816,788

(22) Filed: Mar. 23, 2001

(65) Prior Publication Data

US 2002/0134591 A1 Sep. 26, 2002

(51) Int. Cl.[7] .......................... B01L 3/02; G01G 13/00; G01G 13/10; G01G 13/26
(52) U.S. Cl. ......................... 177/60; 177/116; 177/145; 141/83; 222/55; 222/77; 422/100; 73/864.01; 73/864.11; 73/864.15; 73/864.25
(58) Field of Search .................... 177/60, 116, 117, 177/118, 145; 141/83; 222/55, 56, 77; 73/864.01–864.25; 422/100

(56) References Cited

U.S. PATENT DOCUMENTS

| | | | | |
|---|---|---|---|---|
| 4,974,646 A | * | 12/1990 | Martin et al. ................. | 177/116 |
| 5,006,995 A | * | 4/1991 | Toschi et al. .................. | 222/55 |
| 5,061,639 A | * | 10/1991 | Lung et al. ................... | 422/100 |
| 5,363,885 A | * | 11/1994 | McConnell et al. ........... | 141/83 |
| 5,435,171 A | | 7/1995 | Chino et al. ................. | 73/64.56 |
| 5,492,023 A | | 2/1996 | Kitamura et al. .............. | 73/866 |
| 5,851,491 A | * | 12/1998 | Moulton ...................... | 422/100 |
| 6,132,582 A | * | 10/2000 | King et al. .................. | 422/100 |
| 6,387,330 B1 | * | 5/2002 | Bova et al. .............. | 73/864.01 |
| 6,532,837 B1 | * | 3/2003 | Magussen, Jr. et al. .. | 73/864.14 |

FOREIGN PATENT DOCUMENTS

| | | | |
|---|---|---|---|
| EP | 0 295 035 A2 | 12/1988 | .......... G01G/15/02 |
| EP | 0 556 195 B1 | 9/1991 | |
| WO | WO 92/08964 | 5/1992 | |

* cited by examiner

*Primary Examiner*—Randy Gibson
(74) *Attorney, Agent, or Firm*—Darby & Darby

(57) ABSTRACT

The present invention provides an apparatus for automatically transferring and weighing a powder material. The apparatus comprises a weigh station including a device for weighing the powder material in a container. A transfer device for collecting and dispensing the powder material is provided in which the device has a hollow body having a first end and a second end. The first end being operatively connected to a vacuum source so that a vacuum is selectively formed in the body. A collecting/dispensing tip is detachably coupled to the second end of the body. The tip is a hollow member with a tip orifice at one end so that a vacuum is formed in the tip upon actuation of the vacuum source. A controller for causing the selective actuation of the vacuum source and movement of at least one of the transfer device and the container is provided. The powder material is collected by placing the tip orifice in close proximity to a supply of the powder material resulting in a transfer quantity of powder material being collected in the tip orifice when the vacuum source is actuated. The powder material is transferred to the container by removing the vacuum resulting in the transfer quantity of powder material being dispensed into the container.

34 Claims, 9 Drawing Sheets

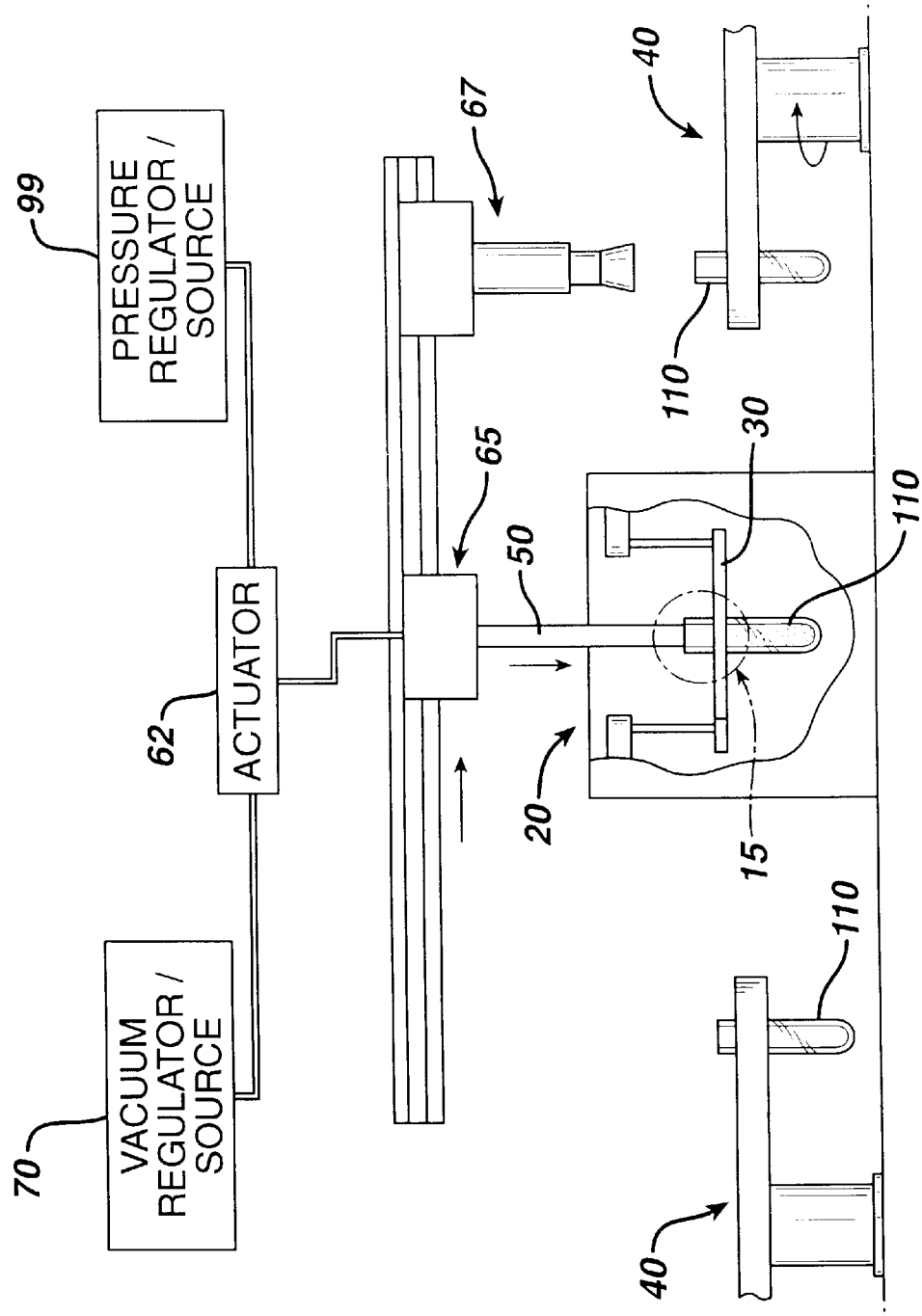

APPARATUS AND METHOD FOR TRANSFERRING AND WEIGHING POWDER MATERIALS USING PIPETTE TRANSFER DEVICES

FIELD OF THE INVENTION

The present invention relates to an apparatus for transferring and weighing materials and, more particularly, to an apparatus for automatically transferring and weighing small quantities of powder materials.

BACKGROUND OF THE INVENTION

One of the most fundamental routines for a chemist is preparation of samples from dry powdered materials. Often times, the chemist is required to measure very small quantities of one or more powders, e.g., on the order of 1–100 mg to form the sample.

Conventional powder dispensing stations are designed around the assumption that a relatively large amount of powder is available for dispensing. Conventional systems for weighing of powders include screw, rotary, vibratory, roll, shaker and revolving plate feeders. More specifically, all of these devices are designed for a large quantity of bulk powder to be continually dispensed into feed lines or vials. Therefore, these devices are not designed to be used in applications where a small quantity of powder is to be weighed. In a similar manner, these devices are not capable of being used when the powder material is contained within a small vial as is the case many times when a chemist or the like needs to weigh a small quantity of powder material.

Conventional powder dispensing and weighing systems also have other associated disadvantages. For example, one of the more common apparatuses for weighing a powder material includes a vibrating feeder provided at an outlet of a hopper for automatically feeding the powder material into a weighing container, e.g., cup or vial, mounted on an electronic weighing device. This type of device is only designed for weighing one kind of powder material. Accordingly, in the case of weighing other kinds of powder materials, it is necessary that the powder hopper is interchanged with other powder hoppers and the vibrating feeder is also interchanged or washed so as not to be mixed or contaminated by the powder material which has been previously weighed. This type of operation requires considerable time and is also costly due to the process being labor intensive.

Furthermore, there are other problems that make it difficult to perfectly prevent the previously weighed powder material from mixing into the next weighing powder material and therefore the accuracy of weighing is not satisfied. This prevents this type of system from being used in applications where a powder material must be weighed without mixing or being contaminated with other powder materials. This is often the case in paint and medicinal applications.

While automated weighing systems for powders have been developed, the success and versatility of many of these systems are in question. Weighing systems for powdery chemicals or medications are generally designed to automatically control the weighing and mixing of the powder so as to prevent the working environment from being contaminated in some instances and to avoid subjecting individuals to prolong exposure to these chemicals. One of the associated disadvantages of this type of conventional system is that the system can be inefficient in conveying powder since each single carrier, for one weighing interval, only can carry a single container to be weighed.

Another disadvantage of conventional powder transfer and weighing systems is that the powder collecting units often do not function effectively. For example, many of these systems include a powder feed pipe which disperses the powder into the container. A dust shield is provided to prevent powder from escaping into the environment, causing contamination thereof, and also to prevent undesired external dust or the like from entering the weighing system. The dust shield includes a powder collecting pipe for collecting floating powder by connecting the collecting pipe to a vacuum so that the powder is sucked through the pipe. Unfortunately, the applied vacuum causes the creation of an air stream within the system and this results in powder being carried away within the air stream to the collecting pipe rather than being dispersed into the weighing container. In addition, powder will accumulate within the collecting pipe by adhering to the internal walls thereof and, over a period of time, this powder will fall into the weighing container, thus affecting the accuracy of weighing.

Other methods for transferring and weighing small quantities of powder material have been proposed. In order to measure small quantities of powder material, instruments are often used which permit an individual to take an apportioned sample of powder material contained in a vial or the like. For example, a weighing instrument which is used to measure small quantities of powder materials is disclosed in International Application PCT/DK91/00288, which is incorporated herein by reference in its entirety. In this application, a pipette is used for taking out an apportioned sample of powder material. The pipette has a split bottom end which may be opened and closed by another suitable device, such as a tool. This instrument is designed to be disposable so that the intended quality of the product is maintained. However, these instruments are not concerned with the weighing of the powder material, but rather comprise instruments that are used to collect, transfer, and dispense the powder material to a weighing receptacle at another station, i.e., an electronic weighing station.

SUMMARY OF THE INVENTION

The present invention provides an apparatus for automatically transferring and weighing a small quantity of a powder material. The apparatus includes a weigh station including a device for weighing the powder material in a container or the like. The apparatus also includes a vacuum source and a transfer device for collecting and dispensing the powder material into the container. In one embodiment, the device is formed of a hollow body having a first end and a second end with the first end being operatively connected to the vacuum source so that a vacuum is formed in the body upon actuation of the vacuum source.

A collecting/dispensing tip is detachably coupled to the second end of the body. The tip is a hollow member with a tip orifice at one end so that a vacuum is formed in the tip upon actuation of the vacuum source and a transfer quantity of the powder material is drawn into the tip orifice. The apparatus also includes a controller for selectively actuating the vacuum source and causing movement of at least one of the transfer device and the container using a robotic device. The controller also monitors the weigh station and measurements thereat. More specifically, the powder material is collected by placing the tip orifice in close proximity to a stock supply of the powder material resulting in a transfer quantity of powder material being collected in the tip orifice when the vacuum source is actuated. The amount of powder material that is drawn into the tip orifice is referred to as the transfer quantity and is defined by several operating parameters of the apparatus. In other words, only a certain amount of powder material is drawn into the orifice tip, namely the amount of powder material which counter balances the vacuum strength. This constitutes the amount of powder material which will be transferred during operation of the apparatus of the present invention.

The powder material is transferred to the container by removing the vacuum resulting in the transfer quantity of powder material being dispensed into the container. The powder material is successively transferred to the container over a number of transfer operations until a target weight is reached. Because the container is preferably disposed on the weighing device, the weight of the container is continuously monitored until the target weight is reached. The controller preferably continuously monitors the transfer operation, including the transfer weight values for each individual transfer, so that the controller automatically determines the number of transfers necessary and also determines whether operation parameters need to be modified so as to alter the average transfer weights in order to achieve the target weight.

The apparatus of the present invention advantageously provides an automated apparatus which is capable of transferring and weighing small quantities of powder material without having the associated disadvantages of the conventional devices.

Other features and advantages of the present invention will be apparent from the following detailed description when read in conjunction with the accompanying drawings.

BRIEF DESCRIPTION OF THE DRAWINGS

The foregoing and other features of the present invention will be more readily apparent from the following detailed description and drawings of illustrative embodiments of the invention in which:

FIG. 14 is a side elevational view, broken away partially, of the apparatus of FIG. 11 showing the robotic transfer device in a second position.

DETAILED DESCRIPTION OF THE PREFERRED EMBODIMENTS

Figure 1:
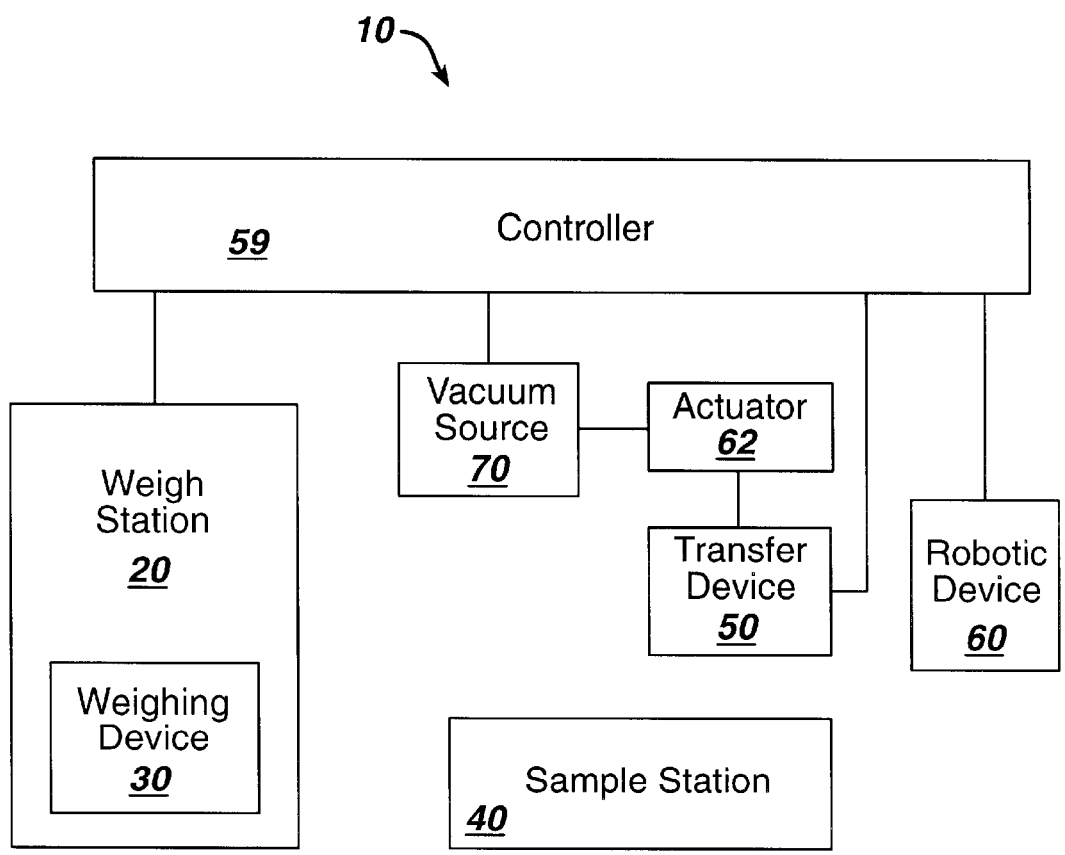
FIG. 1 is schematic block diagram illustrating a transfer and weighing apparatus for a powder material according to one embodiment of the present invention.

FIG. 1 is a schematic block diagram illustrating a transfer and weighing apparatus, generally indicated at 10, according to one embodiment of the present invention for transferring and weighing a powder material. The transfer and weighing apparatus 10 includes a weigh station 20 having a device 30 which is capable of weighing small quantities of powder, e.g., 1–100 mg, within a certain range of accuracy. For example, the weighing device 30 is preferably a weighing scale or electronic balance which is selected in accordance with the desired accuracy from conventional electronic balances which are commercially available. The accuracy and weighing capacity of the weighing device 30 is selected based upon the precise application. For example, the weighing device 30 may be an electronic balance having a maximum weighing value of 200 g and a reading accuracy of 0.1 mg. It will be appreciated that this example is merely illustrative and any type of weighing device 30 may be used in the practice of the present invention. When extremely small quantities of powder are being measured, e.g., on the order of about 0.5–10 mg, it is desirable to employ a weighing device 30 which is very precise and has a high reading accuracy.

The apparatus 10 also includes a sample station 40 which stores a number of powder samples in suitable receptacles, such as a conventional glass vial 100. For example, the sample station 40 may be a wire rack defining a number of compartments which each holds one glass vial filled with a particular powder material. The sample station 40 may also be used to store samples which have been previously weighed at the weigh station 20 according to the present invention. When the sample station 40 includes both receptacles from which the powder is stored and removed for a particular weighing operation and receptacles into which powder material is dispensed, the station 40 may be divided into several different zones.

According to the present invention, the apparatus 10 is an automated transfer and weighing system which is designed to transfer and weigh small quantities of powders from small containers, such as vials. In order to accomplish this, the apparatus 10, in one embodiment, has a transfer device 50 and a robotic device 60 for automating the apparatus 10 as will be described in greater detail hereinafter. The transfer device 50 is broadly a collecting/dispensing assembly which is used to collect a quantity of powder material and then dispense the quantity of powder material into a receptacle which is then weighed at the weigh station 20.

Figure 2:
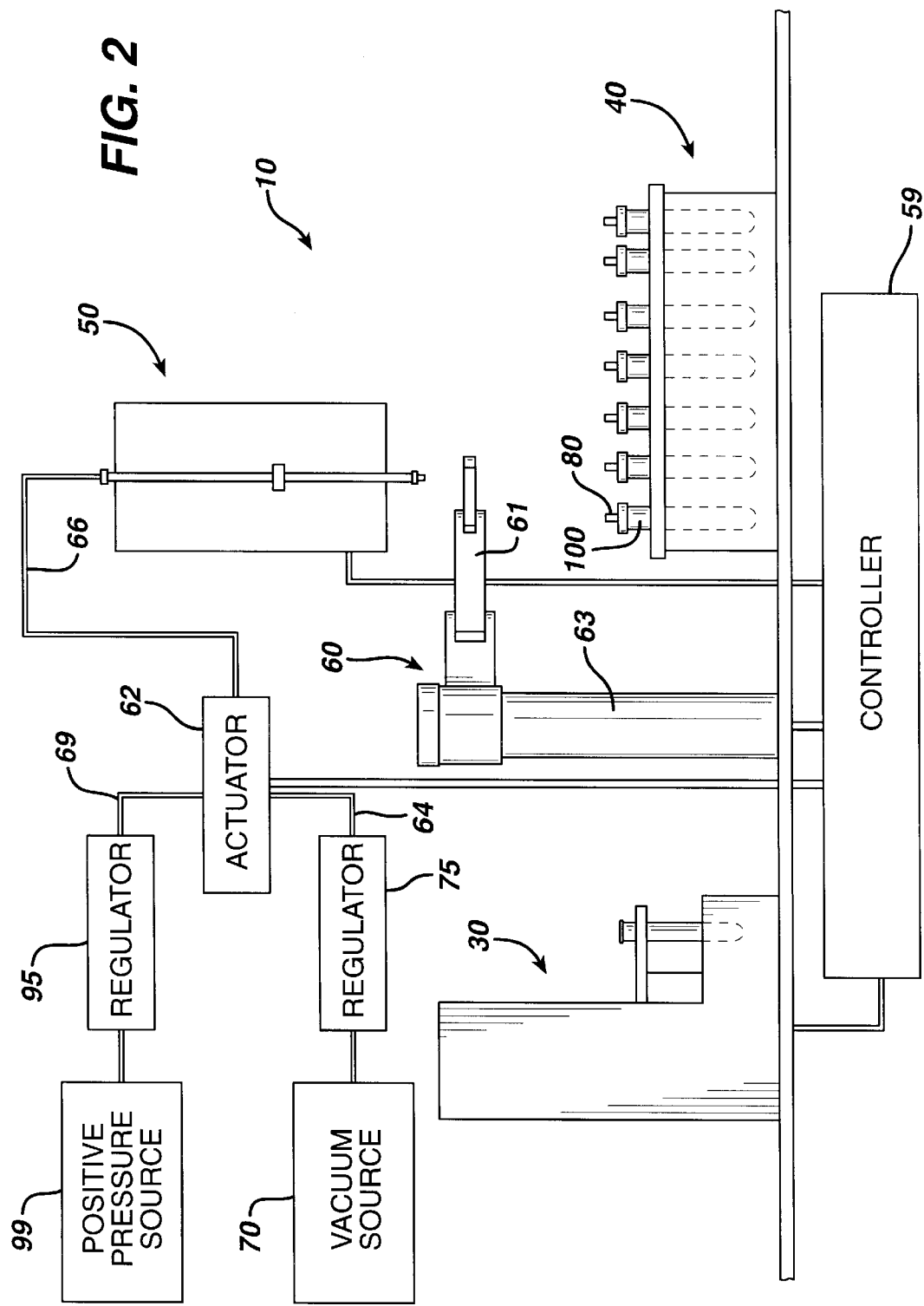
FIG. 2 is a side elevational view of a transfer and weighing apparatus according to one embodiment of the present invention.
Figure 3:
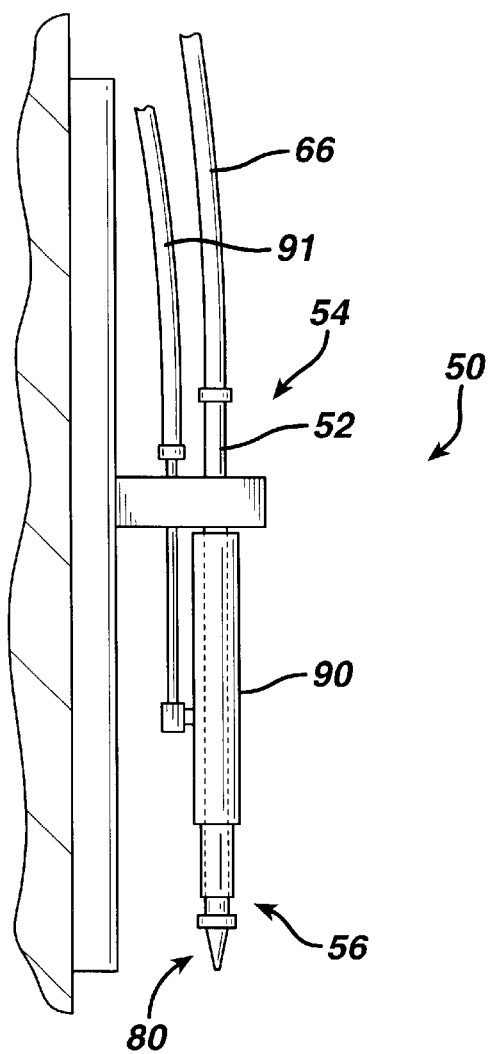
FIG. 3 is an enlarged side elevational view of a collection/dispenser component of the apparatus of FIG. 2.

According to the present invention, the transfer device 50 communicates with a vacuum source, generally indicated at 70, for causing the quantity of powder material to be drawn into and retained (i.e. collected) within the transfer device 50 when the vacuum source 70 is actuated. When the vacuum source 70 is deactivated, the quantity of powder material collected by the device 50 is then dispensed into a corresponding receptacle. The operation of the vacuum source 70 and the transfer device 50 will be further described hereinafter with reference to FIGS. 2–4.

The robotic device 60 is operatively used to deliver and retract receptacle 100 to and from the transfer device 50. The robotic device 60 is positionable between all of the stations of the apparatus 10. For example, the robotic device 60 permits one receptacle 100 to be taken from the sample station 40 and then positioned relative to the transfer device 50 for collecting or dispensing the powder material into the receptacle 100 which then may be delivered to the weigh station 20 by the robotic device 60. Any number of robotic devices may be used and more specifically, the robotic device 60 is preferably a fully programmable laboratory robot designed to provide fast, efficient sample handling operations. One commercial manufacturer of laboratory robots is Zymark Corporation, located at Zymark Center, Hopkinton, Mass. and one exemplary laboratory robot system for use in the present invention is known as the Zymark Benchmate system. The Zymark Benchmate system is designed to handle not only the weighing of solid materials, such as dry powders, but also the weighing of liquids. Accordingly, the weighing device 30 may be operatively connected to a series of syringes (not shown) which store one or more liquids. The syringes are linked to the robotic device 60 so that a predetermined volume of liquid from any one of the syringes may be dispersed upon command. The robotic device 60 thus communicates with mechanical actuators or the like (not shown) which cause the liquid in one or more of the syringes to be dispersed therefrom.

The present invention will now be described in greater detail with reference to FIGS. 1–4. The apparatus 10 also includes a controller 59 which is generally in communication with the robotic device 60, the transfer device 50, the vacuum source 70 and the weigh station 20. The controller 59 may communicate using any number of known communication techniques and it is within the scope of the present invention that the controller 59 may be remotely located from one or more of the devices and communicate using wireless communication techniques or other similar communication methods. The controller 59 will preferably include one or more memory sources and also a central processor which is designed to receive and generate signals for controlling the operation of the robotic device 60, the transfer device 50, the vacuum source 70 and the weigh station 20. It will be appreciated that one or more of these devices may have their own central processing unit associated therewith and in this instance, the controller 59 communicates with this local central processing unit and acts more as a master controller for coordinating all of the actions and operations of the apparatus 10.

The apparatus 10 has an actuator 62 associated therewith for causing selective actuation of the vacuum source 70 such that when the actuator 62 receives a first signal and is actuated, the vacuum source 70 applies a vacuum to the transfer device 50. The actuator 62 thus preferably communicates with the controller 59 and the operation of the vacuum source 70 may be controlled by signals being sent from the controller 59 to the actuator 62. It will be appreciated that the actuator 62 may form a part of the controller 59 or part of the robotic device 60. When the actuator 62 receives a second signal, the actuator 62 is deactivated and the vacuum is removed from the transfer device 50. The actuator 62 may comprise any number of suitable devices such as a valve mechanism and in one embodiment, the actuator 62 is a solenoid valve. For example and according to one exemplary embodiment, the actuator 62 is a three-way solenoid valve.

The actuator 62 may be positioned at a remote location away from other components of the robotic device 60, such as the central processing unit or user interface portion (not shown) thereof. The actuator 62 is sealingly connected to a first line 64 which communicates with the vacuum source 70 and a second line 66 extending therefrom to the transfer device 50 and therefore the lines 64, 66 act to connect the transfer device 50 to the vacuum source 70. The first line 64 may thus be referred to as the vacuum line for the apparatus 10 and the second line 66 is a vacuum line under certain operating conditions. When the apparatus 10 includes the series of syringes (not shown) which store one or more liquids, a syringe line (not shown) may extend between the actuator 62 and the syringes to permit a vacuum to be applied to the syringes in the instance where the syringes are of the type that are vacuum operated. A third line 69 is connected between the actuator 62 and a positive pressure source 99 as will be described in greater detail hereinafter.

The robotic device 60 also has a positionable arm 61 which is adjustable in at least several directions. Preferably, the robotic device is adjustable three dimensionally. For example, the arm 61 has fully independent reach (y axis) and vertical axes (x axis) which provide the flexibility and motion control which is desirable in laboratory systems. Some of the robotic devices (i.e. device 60) which are currently available, and specifically those from Zymark, have interchangeable hands to carry various containers and samples and to perform functions such as gripping and pipetting. These hands are optimized for a specific purpose and several hands may be used throughout one procedure, depending upon the complexity of the procedure. Typically, the robotic device 60 has a base 63 and a track which defines one axis of movement for the robotic arm 61 of the robotic device 60.

The transfer device 50 may be thought of as defining a collecting/dispensing station and is sealingly connected to the second vacuum line 66 which is operatively connected to the vacuum source 70 for selectively applying a vacuum to the transfer device 50 when the actuator 62 is activated. The transfer device 50 has a body 52 having a first end 54 and an opposite second end 56. One end of the vacuum line 66 releasably connects to the first end 54 of the body 52 such that a seal results therebetween. The body 52 has a bore (not shown) formed therein and extending therethrough from the first end 54 to the second end 56. This bore permits air flow therethrough so that upon actuation of the vacuum source 70, air is drawn through the body 52 from the environment surrounding the second end 56. In the exemplary embodiment, the body 52 has a cylindrical shape.

The vacuum source 70 comprises any number of suitable types of vacuum devices which are capable of generating a vacuum in the apparatus 10. For example, the vacuum source 70 may be a vacuum pump which evacuates air through the lines 64, 66. While the strength of the vacuum will depend upon the precise application and equipment used, exemplary vacuum strengths are from about 0 to about 33 mm Hg. It will be appreciated that these values are merely exemplary in nature.

In another aspect of the present invention, a vacuum regulator 75 may be disposed along the line 64 between the vacuum source 70 and the actuator 62. The regulator 75 is designed to regulate the strength of the vacuum source 70 during operation of the apparatus 10. The regulator 75 thus permits the user to input a selected vacuum strength which is created and maintained within the transfer device 50 during actuation of the vacuum source 70. The regulator 75 may be a mechanical device, an electro-mechanical device, or any other type of device and preferably is in communication with the controller 59 so that the selected vacuum strength is stored in memory and continuously monitored. It will be appreciated that the regulator 75 may be placed in other suitable locations. Once the actuator 62 is activated, a negative pressure condition is created in the vacuum lines 64, 66 and the actuator 62 closes the third line 69 so as to prevent positive pressure from being introduced from the positive pressure source 99 to the transfer device 50.

Figure 4:
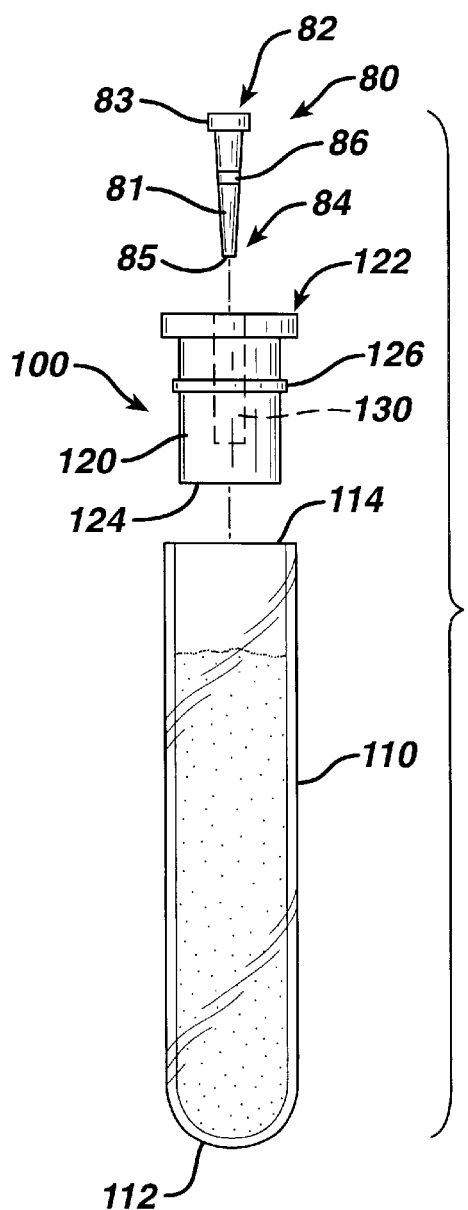
FIG. 4 is an exploded view of a collector/dispenser tip and a capped receptacle of the apparatus of FIG. 2.

A collecting/dispensing tip 80 is detachably connected to the second end 56 of the body 52. In accordance with the present invention, the collecting/dispensing tip 80 defines a cavity 81 having a predetermined volume. As best shown in FIG. 4, one exemplary type of collecting/dispensing tip 80 is a hollow pipette tip which is used to collect and dispense the powder material. The pipette tip 80 is a hollow member generally conical in shape having a first end 82 and an opposing second end 84. The body of the pipette tip 80 tapers toward the second end 84 with the opening formed at the first end 82 having a first diameter and the opening (tip orifice 85) formed at the second end 84 having a second diameter. The second diameter is less than the first diameter and preferably, the second diameter is substantially less than the first diameter. The second end 84 includes the tip orifice 85 which is designed to receive the powder material.

A filter 86 is disposed within the pipette tip 80 and prevents any of the powder material from being inadvertently pulled through the pipette tip 80 into the body 52 toward the vacuum source 70. The filter 86 is of a type commonly used in pipette tips and may be made of either a natural or synthetic material. As shown in FIG. 4, the filter 86 is disposed between the first end 82 and the second end 84. While the pipette tip 80 may be formed of a number of different materials, it is typically formed of a plastic material. This permits the pipette tip 80 to be disposable. Disposability of the pipette tip 80 is desirable because after each collection and dispensing of one type of powder material, the pipette tip 80 must be changed before the transfer device 50 is used to collect and dispense another type of powder.

It will be understood, that any number of other types of collecting/dispensing tips 80 may be used according to the present invention. For example, any hollow member which has a small diameter opening at one end may be used to collect and dispense the powder material so long as the member is capable of being used in the present apparatus 10 and provides the desired operation characteristics described hereinbefore.

An ejector, generally indicated at 90, is preferably included in the transfer device 50 to selectively eject the pipette tip 80 from the second end 56 of the body 52 after the pipette tip 80 is fully used. In one embodiment, the ejector 90 is a shucking device which is operatively coupled to the body 52 of the transfer device 50 to cause the pipette tip 80 to be ejected upon activation of the ejector 90. In other words, the ejector 90 may be in the form of a sleeve which is disposed around the body 52 and is in communication with a controller, such as the CPU in the robotic device 60, such that the sleeve 90 is selectively moved along the body 52 toward the second end 56. The first end 82 of the pipette tip 80 preferably has a diameter which is greater than the diameter of the sleeve 90 so that upon being displaced toward the second end 56, the sleeve 90 contacts and causes the pipette tip 80 to be displaced from the body 52. The sleeve 90 is then retracted to its pre-activation position to permit another pipette tip 80 to be placed at the second end 56 of the body 52.

It will be appreciated that the ejector 90 may be controlled by its own separate controller or it may be operatively connected to the controller 59 or the robotic device 60 via line 91. In addition, it will also be appreciated that the robotic arm 61 may be designed to cause the sleeve 90 to be displaced along the body 52 so as to cause the selective ejection of the pipette tip 80.

FIG. 4 illustrates a capped receptacle (container) 100 formed by a body 110 and a cap 120. The body 110 is hollow and closed at one end 112 and open at another end 114. While any number of types of receptacles (containers) may be used, the body 110 is preferably a standard glass vial which holds the powder material. According to the present invention, the cap 120 is specially designed to be used with the other components of the apparatus 10. More specifically, the cap 120 has a partially open end 122 and an opposing closed end 124. Between the ends 122, 124, an annular shoulder 126 is provided and acts as a stop to prevent the cap 120 from being completely inserted into the body 110.

A bore 130 is formed in the cap 120 and extends along a length of the cap 120 but does not extend completely therethrough. The bore 130 has a diameter which preferably accommodates a significant portion of the pipette tip 80 so as to permit the pipette tip 80 to be inserted and held therein. The pipette tip 80 preferably has an annular shoulder 83 which has a diameter which is greater than the diameter of the bore 130. This causes the annular shoulder 83 to act as a stop and prevent the pipette tip 80 from being completely inserted into the bore 130. When the pipette tip 80 is inserted into the bore 130, a portion 85 of the pipette tip 80 protrudes beyond the first end 122 of the cap 120. This portion 85 includes the first end 82 of the pipette tip 80. The robotic arm 61 of the robotic device 60 may grip and easily remove the pipette tip 80 from the cap 120 by gripping the portion 85.

The bore 130 thus defines an area which receives and conveniently holds the pipette tip 80 prior to performing a weighing operation. This provides an attractive and effective manner of packaging the capped receptacle 100 with one pipette tip 80. Each capped receptacle 100 and more specifically, each powder material contained therein, has one pipette tip 80 which is associated therewith so that the robotic arm 61 can easily first remove the pipette tip 80 from the cap 120 and then place the pipette tip 80 on the body 52 before removing the cap 120 from the body 110. A weighing operation may now proceed once the body 110 is uncapped and the powder material is accessible.

The operation of the controller 59 and the actuator 62 and the robotic device 60 generally constitute a mechanism for controlling the apparatus 10 according to the present invention for causing the selective actuation of the vacuum source and the movement of at least one of the transfer device 50 and the capped receptacle 100.

The operation of the apparatus 10 will now be described in greater detail. According to the present invention, an automated method of transferring and weighing powder materials is presented in which small quantities of powder material may be transferred to the weighing station 20 from small containers, such as conventional vials (receptacles 100). First, a powder is selected for transfer and a target weight is selected. The target weight of the sample is the quantity of the powder material which is to be collected from a stock supply of the powder material. Because of the design of the present invention, the stock supply may be contained in a conventional glass vial, such as body 110, which may have a small diameter, e.g., 0.5 inch inner diameter. It will be appreciated that the target weight will vary from application to application; however, one exemplary range of target weights for use with the apparatus 10 of the present invention is from about 1 mg to about 100 mg. It will be appreciated that these target weights are merely illustrative and a particular target weight for a given application may be outside of this range.

Because the apparatus 10 is preferably an automated apparatus, the controller 59 or the robotic device 60 itself will have a user interface component which permits a user to enter certain information prior to the system 10 performing a particular operation. For example, the user may enter the type of powder to be weighed and the target weight on a keyboard or the like. In addition, the user may enter the particle size of the powder material. Based upon the information inputted, the controller 59 and/or the robotic device 60 will then select the most efficient and accurate manner of transferring the powder material such that the target weight will be achieved. For example, if the user enters that the target weight is only 1 mg, the controller 59 or the CPU of the robotic device 60 will compute that a small diameter pipette tip 80 should be used as this will cause less powder material to be transferred based upon the powder collection process, as will be described hereinafter. In other words, the controller 59 is fully programmable so that the transferring operation and subsequent weighing operation proceed based partially upon information already programmed into the controller 59 and the information inputted by the user. It will also be appreciated the robotic device 60 is also preferably fully programmable and therefore, the robotic device 60 is capable of calculating how the weighing operation should proceed.

Figure 5:
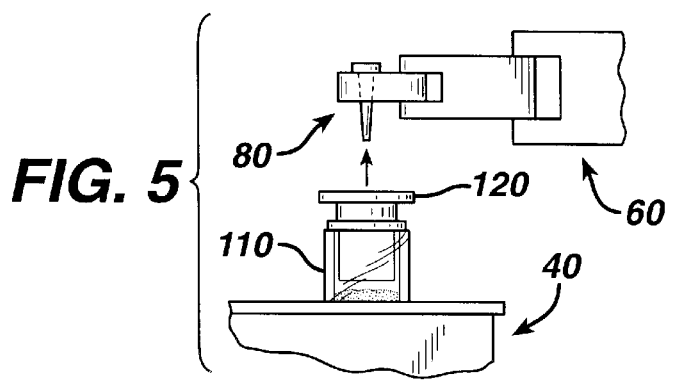
FIG. 5 is a side elevational view of the apparatus of FIG. 2 in a first position where the collector/dispenser tip is removed from the receptacle by a robotic device.
Figure 6:
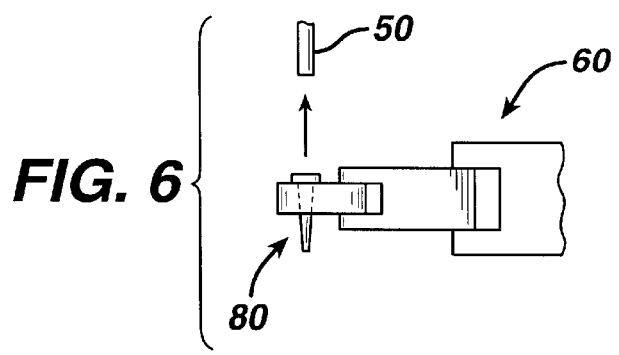
FIG. 6 is a side elevation view of the apparatus of FIG. 2 in a second position showing the collector/dispenser tip being delivered to a transfer device.
Figure 7:
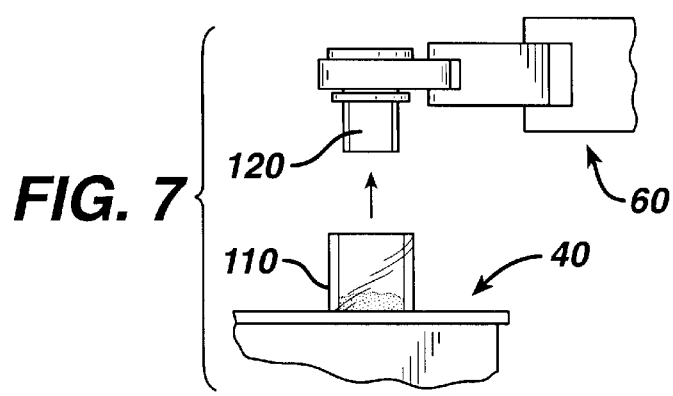
FIG. 7 is a side elevation view of the apparatus of FIG. 2 in a third position showing a cap being removed from the receptacle.

The robotic device 60 will then communicate with the robotic arm 61 and cause the arm 61 using known coordinated systems to be positioned relative to the proper capped receptacle 100 which contains the selected powder material. The position of the robotic arm 61 is continuously monitored using conventional robotic software which is included as part of the robotic device 60. Because the controller 59 is in continuous communication with the robotic device 60, the controller 59 knows the precise position of the robotic arm 61 and can signal and direct the robotic device 60 to position the robotic arm 61 as need be during the transfer and weighing operation. As shown in FIGS. 5 and 6, the pipette tip 80 is removed from the bore 130 and then placed onto the second end 56 of the body 52 so that the pipette tip 80 is securely retained thereon. The cap 120 is removed from the body 110 to permit access to the powder material contained within the body 110 as shown in FIG. 7.

Figure 8:
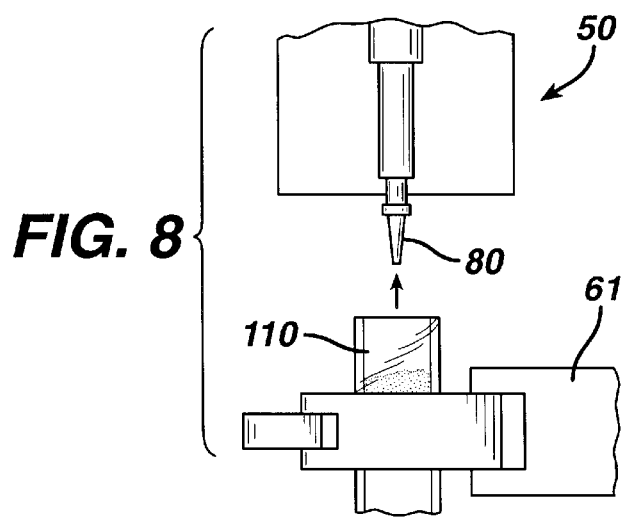
FIG. 8 is a side elevation view of the apparatus of FIG. 2 in a fourth position showing the uncapped receptacle being delivered to the transfer device.
Figure 9:
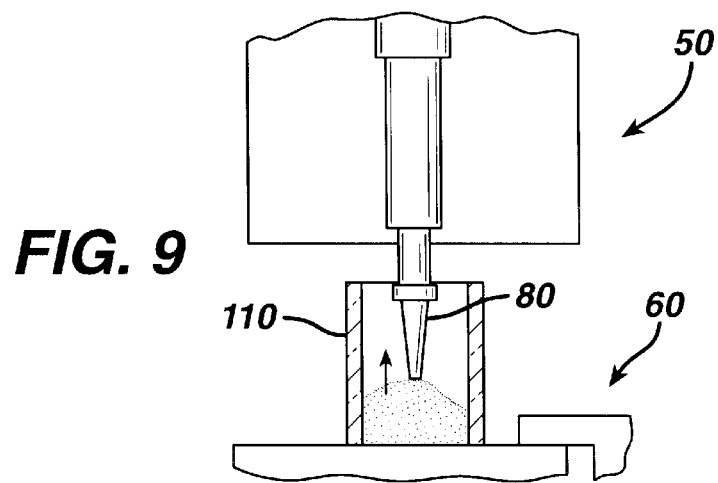
FIG. 9 is a side elevation view of the apparatus of FIG. 2 in a fifth position showing the pipette tip disposed within the receptacle containing a powder and the collection of an amount of the powder by actuation of the apparatus.

As shown in FIG. 8, the robotic arm 61 grips the body 110 containing the powder material and delivers the body 110 to the transfer device 50 such that the pipette tip 80 is aligned with the interior to the body 110. The controller 59 is programmed so that the body 110 is advanced upwardly until the pipette tip 80 enters the open end 114 of the body 110. More specifically, the body 110 is positioned relative to the pipette tip 80 such that the pipette tip 80 is positioned proximate to the powder material contained within the body 110, as shown in FIG. 9.

The actuator 62 is then actuated causing a vacuum condition within the lines 64, 66. As previously-mentioned, the actuator 62 is preferably in communication with the controller 59 so once the controller 59 determines that the pipette tip 80 is in the correct position, it will signal the actuator 62 to apply the vacuum to the pipette tip 80. It will be appreciated that the vacuum condition may be formed in the lines 64, 66 prior to inserting the pipette tip 80 into the powder material. A vacuum condition results also in the cavity 81 of the pipette tip 80 because the pipette tip 80 is connected to the vacuum source 70. When the pipette tip 80 is placed into the powder material, a small quantity of powder material will be drawn into the orifice 85 of the pipette tip 80. In other words, the vacuum draws a small quantity of the powder material into the orifice 85 so as to clog the orifice 85. The quantity of powder material that is collected is preferably only that amount of powder material which counter balances the vacuum. Once, the orifice 85 is clogged, additional powder material may not be drawn into the pipette tip 80 through the orifice 85. The amount that is present in the orifice 85 is thus the transfer weight of the powder material (the quantity to be transferred to the receptacle which collects the powder material to be weighed).

The quantity of powder material which is drawn into the orifice 85 depends upon several parameters. For example, the vacuum strength (vacuum pressure) of the vacuum source 70 varies the quantity of powder material which may be retained within the pipette tip 80 under application of the vacuum. For example, a greater vacuum pressure permits a greater quantity of powder material to be retained by the pipette tip 80. In addition, the diameter (or size) of the orifice 85 also affects the quantity of powder material which may be retained by the pipette tip 80. For example, if the vacuum strength is held constant and the diameter of the orifice 85 is decreased, the pressure flow of air through the orifice 85 in response to actuation of the vacuum source 70 is increased. However, the surface area of the orifice 85 has decreased and therefore the powder material more easily clogs the orifice 85. This results in less powder material being retained within the pipette tip 80. In other words, the transfer weight of the powder material is less. Another parameter which affects the quantity of powder material that may be transferred using a specific vacuum pressure (vacuum strength) is the particle size of the powder material. A greater particle size will likely cause the transfer weight to be reduced as compared with other powder materials having smaller particle sizes (assuming the vacuum pressure is the same and the size of pipette tip 80 is constant). The controller 59 is also preferably in communication with the vacuum source 70 and the regulator 75 so that the controller 59 may signal the regulator 75 to either increase or decrease the strength of the applied vacuum.

Figure 10:
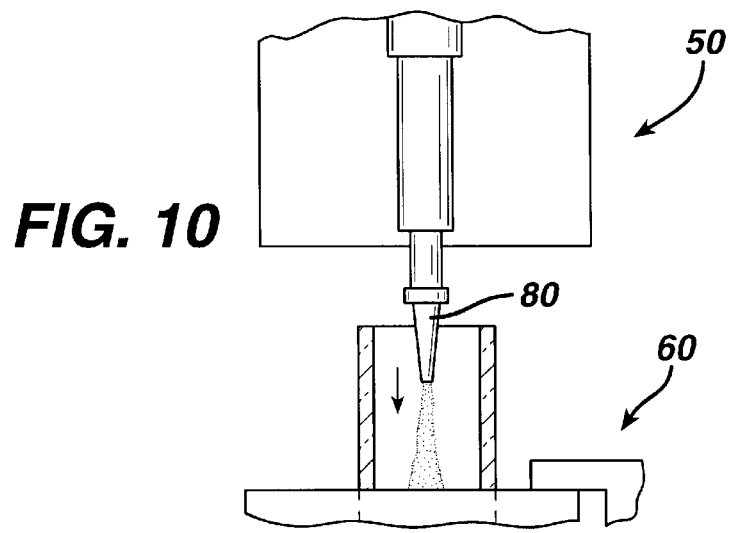
FIG. 10 is a side elevation view of the apparatus of FIG. 2 in a sixth position showing the receptacle with power being moved away from the transfer device with the pipette tip retaining an amount of powder under actuation of powder.

After the powder material is collected within the orifice 85, the body 110 is then removed away from the pipette tip 80. The robotic device 60 then retrieves an empty collection receptacle body 110 from the station 40 or some other station and the process is partially repeated where the robotic device 60 brings the body 110 up to the transfer device 50. The receptacle body 110 is positioned so that the pipette tip 80 is preferably within the walls of the body 110. Throughout the positioning of the empty receptacle body 110, the vacuum source 70 remains actuated, thereby maintaining the vacuum pressure in the apparatus 10. After the pipette tip 80 is properly positioned within the body 110, the controller 59 and/or the robotic device 60 signals the actuator 62 to remove the vacuum to the pipette tip 80. The actuator 62 is thus deactivated, thereby preventing vacuum pressure from being applied to the transfer device 50, including the pipette tip 80. Once the vacuum is removed, the powder material that has been collected in the orifice 85 is dispensed and falls into the collection receptacle body 110 as shown in FIG. 10.

It is also within the scope of the present invention, that the apparatus 10 may be designed to generate a slight positive pressure through the transfer device 50 and more specifically through the pipette tip 80 as to facilitate the dispensing of the powdered material after the vacuum is removed. This may be accomplished in any number of different ways. The slight positive pressure is preferably generated by the positive pressure source 99 which is connected to the actuator 62 using the third line 69. Preferably, a second regulator 95 is provided for regulating the level of positive pressure introduced to the transfer device 50. Once again, the regulator 95, similar to the regulator 75, is designed so that the user selects and enters into the second regulator 95 the amount of positive pressure to be applied once the actuator 62 opens the third line 69. In one exemplary embodiment, the positive pressure is from about 0 to about 10 psi. The regulator 95 is preferably in communication with the controller 59 and in one exemplary embodiment, the controller 59 may be used to change the amount of positive pressure applied to the transfer device 50. To generate the positive pressure, the user simply instructs the controller 59 to remove the applied vacuum and apply a positive pressure instead of the negative pressure associated with the operation of the vacuum source 70. In response to signal commands from the controller 59, the actuator 62 closes the line 64 and opens the third line 69 so as to produce a positive pressure in the line 66 connected to the transfer device 50. This results in any remaining powder material being dispensed.

After the powder material has been dispensed and collected into the collection receptacle body 110, the robotic device 60 moves the collection body 110 away from the pipette tip 80 of the transfer device 50 until the open end 114 of the body 110 clears the pipette tip 80. The collection body 110 is then delivered to the weight station 20 by the robotic device 60 and is disposed on the weighing device 30. The transfer weight of the powder material is then easily determined. The weighing device 30 is integrated into the overall apparatus 10 so that the measured weight of the dispensed powder material is continuously determined and is delivered to the controller 59 which stores this information in memory. It will be appreciated that the robotic device 60 may be designed so that the robotic device 60 receives the weighing information and processes it accordingly. The collection and dispensing process is simply repeated until the target weight is achieved. Each time a quantity of powder material is transferred to the collection receptacle body 110, the apparatus 10 monitors the transfer weight for each successive transfer and based upon this information, calculates the number of transfers which are required in order to obtain the target weight. This operation will be done by the controller 59 and/or the robotic device 60. For example, if the target weight is 6 mg and the first two transfers delivered 4 mg to the collection body 110, the controller 59 will calculate that one additional transfer is necessary to reach the target weight of 6 mg.

The present apparatus 10 is designed to compute average transfer weights so that even if the transfer weights for individual transfers differ from one another slightly, the apparatus 10 preferably computes an average transfer weight and then determines the number of additional transfers that are required to reach the target weight. The average transfer weight is continuously determined by the controller 59 is preferably displayed on a display (not shown) thereof.

Because the user inputs many of the important parameters, the apparatus 10 is capable of computing how the transfer and weighing process should proceed. Furthermore, the apparatus 10 is also able to adapt as the process proceeds in order to reach the target weight. For example, if the apparatus 10 calculates that, in order to reach the target weight, a quantity of powder material is needed which is less than the average transfer weight, the apparatus 10 will compensate by undertaking one or more actions. For example, the pipette tip 80 may be replaced with a pipette tip 80 having a smaller diameter so that a smaller transfer weight may be achieved. In addition or alternatively, the vacuum strength (vacuum pressure) may be adjusted so that less powder material is collected resulting in a smaller transfer weight. Other parameters of the apparatus 10 may be adjusted in order to obtain the necessary transfer weight to achieve the target weight. In one exemplary embodiment, the transfer weight is from about 0–10 mg depending upon the precise application and the target weight which is to be achieved. It will be understood that these values are merely exemplary in nature and an individual transfer weight may be outside of this range.

In addition, if the user inputs that the sample to be weighed includes more than one powder material, the controller 59 will first weigh the first powder material and then will proceed with weighing the second powder material. Because the measured weight of the first powder material is stored in memory, the controller 59 is capable of determining how much of the second powder material has been added subsequent to the transfer and weighing of the first powder material. This permits the controller 59 to continuously and separately monitor the weights of the first and second powder materials.

The above-described apparatus 10 is easily modified, in part, because it is an automated process. The location of the various stations and the precise manner of collecting and dispensing powder material may be modified. For example, a second embodiment is shown in FIGS. 11–15. In this embodiment, the robotic device actually comprises a first transfer robotic device 65 for collecting and transferring the powder material and a second robotic device 67 for transferring one or more receptacle bodies 110.

Figure 11:
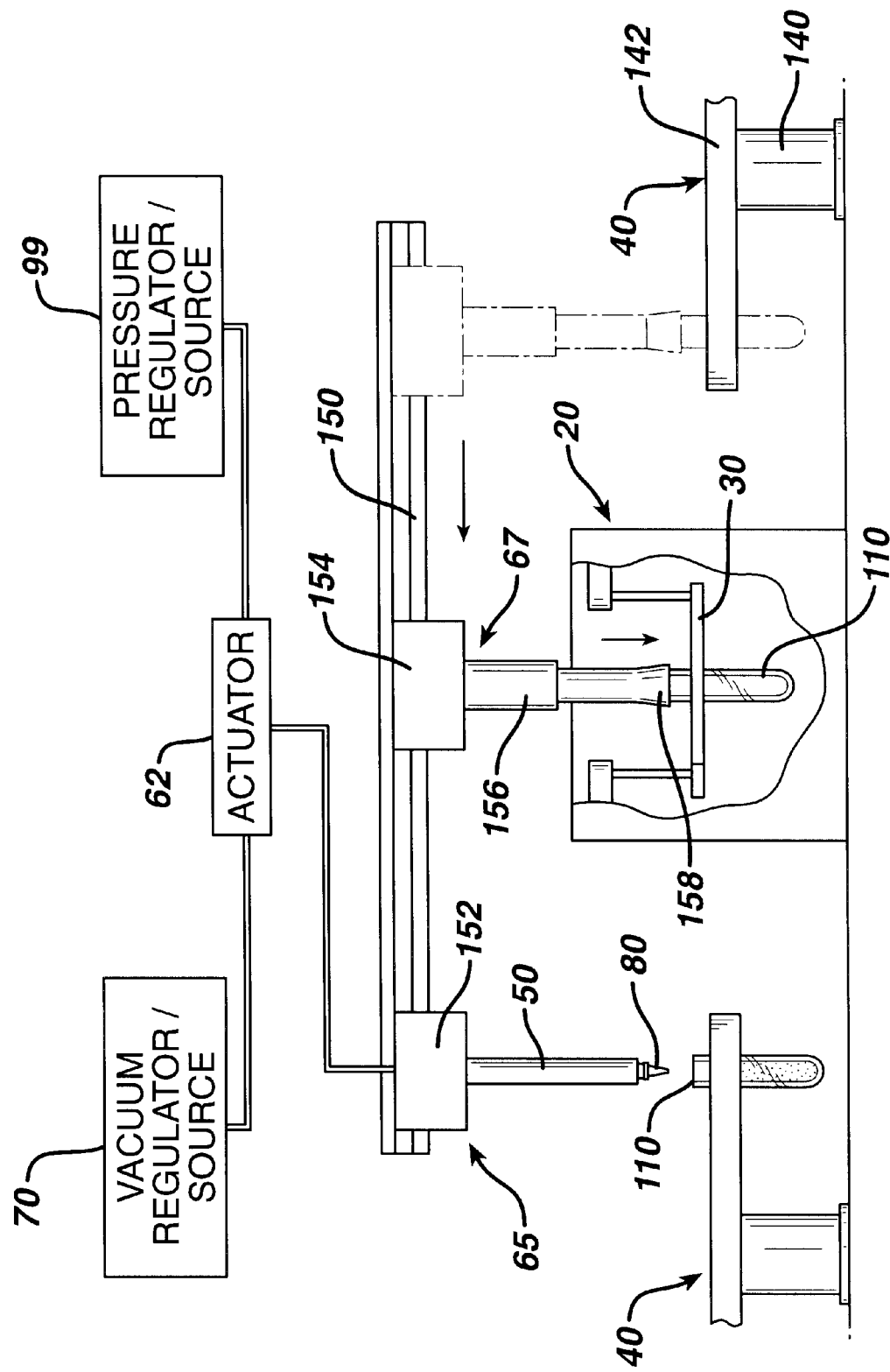
FIG. 11 is a side elevational view, broken away partially, of a transfer and weighing apparatus according to a second embodiment of the present invention showing a secondary robotic device in a first position.

In this embodiment, there are two sample stations 40 which each preferably is in the form of a programmable turntable having an indexing systems associated therewith. The turntable sample station 40 includes a base 140 is operatively driven by a motor or the like (not shown) to cause controllable rotation of a planar platform 142 which is connected to the base 140. The platform 142 has a number of openings (not shown) formed therein for receiving the receptacles 100. As shown in FIG. 11, the weight station 20 is positioned between the two turntable sample stations 40.

Both the first transfer robotic device 65 and the second robotic device 67 preferably move along a track 150 which extends between the turntable sample stations 40 and across the weigh station 20. The first robotic device 65 incorporates the transfer device 50 in that the transfer device 50 extends outwardly from a base 152 of the first robotic device 65. The second robotic device 67 also has a base 154 but has an arm 156 extending outwardly therefrom which is operative to retain one receptacle body 110 so that the body 110 may be moved to any number of other station locations.

FIG. 11 shows the second robotic device 67 in action as it moves from a first location shown in phantom to a second location. In the first location, the second robotic device 67 is positioned above the nearest turntable sample station 40. This station 40 preferably holds a number of empty receptacle bodies 110. In one embodiment, the second robotic device 67 is selectively connected to a vacuum source, such as vacuum source 70. A head 158 of the arm 156 has a complementary shape relative to the open end of the body 110 and partially receives the open end as shown in FIG. 11. When an actuator, such as actuator 62, is activated, a vucuum is applied through the arm 156 and head 158 causing the open end of the body 110 to be drawn slightly into the head 158 and securely retained therein by the force of the vacuum. The second robotic device 67 is then moved to its second position where the second robotic device 67 is manipulated so as to dispose the empty collection body 110 within the weighing device 30.

The first robotic device 65 functions similar to the combined robotic device 60 and transfer device 50 of the first embodiment except that in this embodiment, the transfer device is brought to the powder material disposed within the receptacle body 110 stored at the turntable sample station 40. The first robotic device 65 is connected to the positive pressure source 99 and the vacuum source 70 as well as the actuator 62. The turntable sample station 40 that is below the first robotic device 65 preferably includes a number of receptacle bodies 110 each containing a different powder material. The turntable sample station 40 preferably has an indexing system such that the rotation of the station 40 may be timed along with the movements of the first robotic device 65 such that after one powder material is collected by the first robotic device 65, the station 40 rotates and a different body 110 is then positioned underneath the first robotic device 65. Preferably, the indexing system is fully integrated and programmable so that movements of both of the turntable sample stations 40, the first robotic device 65 and the second robotic device 67 are coordinated. One will appreciate that the second robotic device 67 is used to remove the collection body 110 after the powder material has been dispensed therein.

Figure 12:
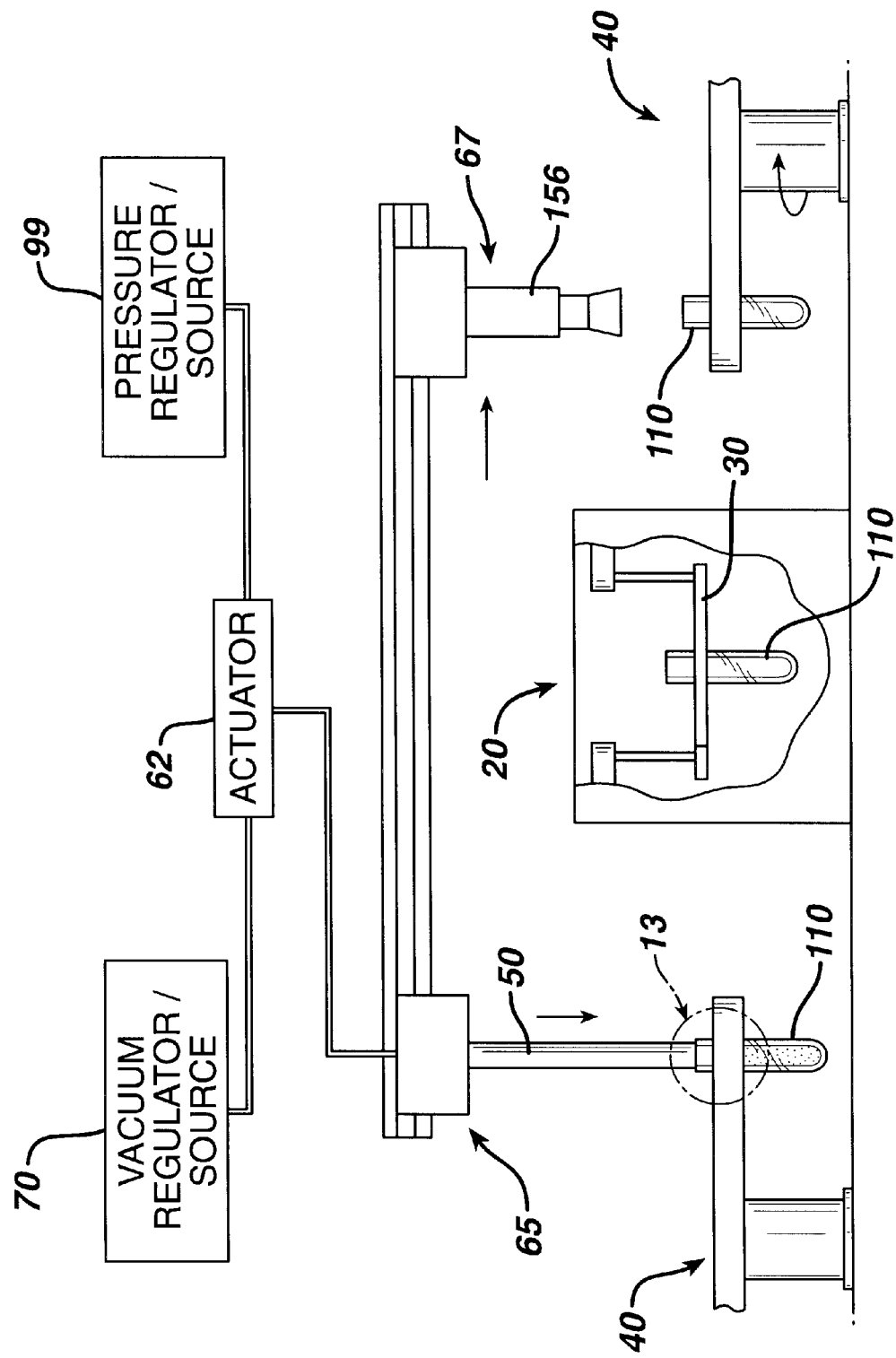
FIG. 12 is side elevational view, broken away partially, of the transfer and weighing apparatus of FIG. 11 showing the secondary robotic device in a second position.
Figure 13:
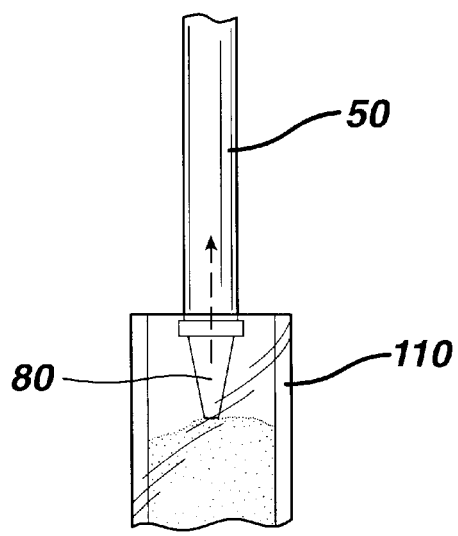
FIG. 13 is an enlarged partial view of a robotic transfer device of the apparatus of FIG. 11 in a first position collecting powder from a receptacle.
Figure 15:
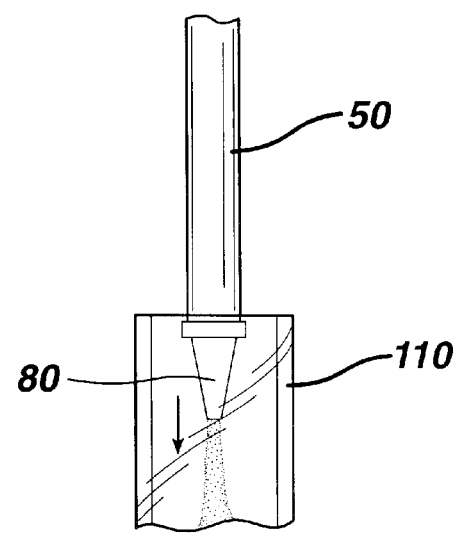
FIG. 15 is an enlarged partial view of the robotic transfer device dispensing the collected powder within the receptacle.

The first robotic device 65 collects and dispenses the powder material. The transfer device 50 and more particularly, the pipette tip 80 thereof, is positioned over the target receptacle body 110 containing the powder material. This is preferably done using the controller 59 (FIG. 2) and by programming the entire apparatus, the actions may proceed in an automated manner. The pipette tip 80 is positioned within the interior of the receptacle body 110 and then the actuator 62 is activated so that a vacuum is applied to the pipette tip 80, similar to the first embodiment as shown in FIGS. 12 and 13. The collection and dispensing process proceeds in relatively the same manner as in the first embodiment in that after the powder material is collected, the transfer device 50 is moved so that the pipette tip 80 holding the powder material is positioned over and preferably at least partially within the interior of the collection body 110 located at the weighing device 30 as shown in FIGS. 14 and 15. The vacuum is then released causing the powder material to be released into the collection body 110. The process is repeated until the collection body 110 contains the desired amount of powder material.

Referring back to the first embodiment, one of skill in the art will appreciate that the robotic device 60 may be designed so that it moves the transfer device 50 to and from the receptacle bodies 100 that are disposed in one or more of the sample station 40 and the weigh station 20. The robotic device 60 then positions the transfer device 50 over the collection receptacle 100 and upon releasing the vacuum, the powder material is dispensed. If the collection receptacle body 110 is not disposed on the weighing device 30, the robotic device 60 may be programmed to grasp the collection receptacle body 110 after the powder material has been dispensed therein and place the body 110 on the weighing device 30 for weighing thereof. This increases the versatility of the apparatus.

The apparatus according to any of the embodiment of the present invention provides numerous advantages over conventional transfer and weighing systems. First, the safety of the user is protected because the apparatus is a fully automated process which does not require the user to be exposed to any of the powder materials during the transfer and weighing process. In conventional systems, the user would be exposed to the entire process. Second, the apparatus is a tunable system in which the transfer weight is tuned so as to achieve the target weight after one or more transfers have been made. As previously mentioned, the transfer weight may be "tuned" (i.e. adjusted) by varying one of a number of parameters, such as adjusting the orifice size of the pipette tip 80 or by adjusting the vacuum pressure. Third, the present system overcomes the problems associated with powder lumps. Typically, powder materials contain some lumps which complicate the transfer and weighing process. Because the apparatus of the present invention by design picks up only enough material to counter balance the vacuum, lumps are not transferred. More specifically, the lumps have significant associated masses and sizes and the orifice 85 of the pipette tip 80 is designed to only pick up small quantities of material. Thus, the apparatus effectively and advantageously does not pick up large masses, such as lumps.

Fourth, the apparatus provides a relatively inexpensive design because the system uses inexpensive components, such as solenoids 62 and disposable pipette tips 80. Fifth, the apparatus is automation friendly. Because the system uses inexpensive and automation friendly components, the apparatus can be incorporated onto various robotic platforms without a lot of additional cost. Sixth, weights are electronically captured adding robustness to the overall sample preparation. Seventh, the speed of the apparatus can be optimized to meet that of the manual method.

While the invention has been particularly shown and described with reference to the preferred embodiments thereof, it will be understood by those skilled in the art that various changes in form and details may be made therein without departing from the spirit and scope of the invention.

What is claimed is:

1. An apparatus for automatically transferring and weighing a powder material, the apparatus comprising:
    a weigh station including a device for weighing the powder material in a container;
    a selectively actuatable device for generating a vacuum;
    a transfer device for collecting and dispensing the powder material, the transfer device being operatively connected to the vacuum device so that a vacuum is formed in the device upon actuation of the vacuum source, wherein the vacuum device is disposed external to the transfer device;
    a collecting/dispensing tip detachably coupled to one end of the transfer device, the tip being a hollow member with a tip orifice at one end so that a vacuum is formed in the tip upon actuation of the vacuum device;
    a controller for causing the selective actuation of the vacuum device and movement of at least one of the transfer device and the container; and
    a regulator for regulating the strength of the vacuum source, wherein the powder material is collected by placing the tip orifice in close proximity to a supply of the powder material resulting in a transfer quantity of powder material being collected in the tip orifice when the vacuum device is actuated, the powder material being transferred to the container by removing the vacuum resulting in the transfer quantity of powder material being dispensed into the container.

2. The apparatus of claim 1, wherein the powder material is repeatedly transferred to the container until a target weight is reached.

3. The apparatus of claim 1, wherein the weighing device is an electronic weighing device.

4. The apparatus of claim 1, wherein the vacuum device includes a vacuum pump for generating a vacuum pressure in the transfer device.

5. The apparatus of claim 1, wherein the collecting/dispensing tip is a pipette tip.

6. The apparatus of claim 5, wherein the pipette tip is a hollow conical member having a first opening at a first end and a second opening at a second end.

7. The apparatus of claim 6, wherein the first opening has a first diameter significantly less than a diameter of the second opening.

8. The apparatus of claim 5, wherein the pipette tip has a filter disposed therein to prevent the powder material from flowing into the transfer device and into the vacuum device.

9. The apparatus of claim 1, wherein the collecting/dispensing tip including the tip orifice define the transfer quantity of the powder material which is collected under application of the vacuum.

10. The apparatus of claim 1, wherein the controller includes a robotic device for automating operation of the apparatus and permitting multiple transfers of the powder material from the powder material supply to the container.

11. The apparatus of claim 1, wherein the controller includes a valve member for selectively actuating the vacuum device.

12. The apparatus of claim 11, wherein the valve member is a solenoid valve.

13. The apparatus of claim 1, wherein the controller includes a robotic device having a robotic arm for gripping and positioning the transfer device and the container relative to one another.

14. The apparatus of claim 1, wherein the transfer quantity is less than about 10 mg.

15. The apparatus of claim 1, where the transfer quantity is varied by varying one of a diameter of the tip orifice and a vacuum pressure of the vacuum source.

16. The apparatus of claim 1, wherein the container is a vial having a cap with an opening configured to receive a portion of the collecting/dispensing tip.

17. The apparatus of claim 1, wherein the controller communicates with the weighing device so that a measured weight of the powder material is continuously determined by the weighing device and processed by the controller.

18. The apparatus of claim 1, wherein the controller includes a user interface for inputting user information including a target weight and a diameter of the orifice tip.

19. The apparatus of claim 18, wherein the controller is configured so that it continuously computes the number of transfers needed to reach the target weight based upon the user input information and then generates control signals instructing the transfer device as how to continue with any needed additional transfers.

20. The apparatus of claim 1, wherein the transfer quantity is an amount of powder material needed to counter balance a strength of the vacuum source measured in terms of vacuum pressure.

21. The apparatus of claim 1, further including:
an ejector coupled to the body of the transfer device for causing the selective ejection of the collecting/dispensing tip.

22. The apparatus of claim 21, wherein the ejector is in communication with the controller which signals the ejector to cause displacement of the ejector along the body and ejection of the tip from the second end of the body.

23. The apparatus of claim 1, wherein the ejector is a shucker concentrically disposed around a length of the body.

24. The apparatus of claim 1, wherein the vacuum strength is less than about 30 mm Hg.

25. The apparatus of claim 1, further including:
an external device for generating positive pressure selectively connected to the transfer device an in communication with the controller so that the powder material is fully dispensed when the vacuum is removed and positive pressure is applied to the transfer device.

26. A method of automatically transferring and weighing a powder material, the method comprising:
providing a transfer device for collecting and dispensing the powder material, the transfer device including a collecting/dispensing tip and being operatively connected to a vacuum source;
actuating the vacuum source so that a vacuum is formed in the collection/dispensing tip;
positioning the collecting/dispensing tip relative to a supply of the powder material causing a transfer quantity to be drawn into the tip due to the resultant vacuum;
regulating the strength of the vacuum source;
positioning the tip relative to a collection container and removing the vacuum from the tip, thereby causing the transfer quantity of powder material to be dispensed into the collection container;
weighing the powder material using a weighing device; and
repeating, as necessary, the transfer of the powder material into the collection container until a target weight for the powder material is reached.

27. The method of claim 26, wherein the positioning of the collecting/dispensing tip is done by a programmable robotic device.

28. The method of claim 26, wherein drawing the transfer quantity of powder material into the tip comprises:
drawing an amount of the powder material which counter balances a strength of the vacuum as measured in terms of vacuum pressure.

29. The method of claim 26, wherein drawing the transfer quantity of powder material into the tip comprises:
drawing an amount of the powder material into a tip orifice until the tip orifice becomes clogged.

30. The method of claim 26, wherein the transfer quantity is varied by varying one of a diameter of the tip orifice and a vacuum pressure of the vacuum source.

31. The method of claim 26, further including:
controlling the operation of the transfer device, the vacuum source and the weighing device using a controller which is in communication therewith, the controller being programmable so that input information may be inputted.

32. The method of claim 26, wherein removing the vacuum comprises sending a signal to an actuator which is operatively connected to the vacuum source and the transfer device, whereupon receiving the signal, the actuator removes the vacuum from the tip.

33. The method of claim 32, wherein the actuator comprises a solenoid valve.

34. The method of claim 31, wherein the controller receives a signal from the weighing device representative of the current weight of the powder material in the collection container, the controller processing the signal and calculating a number of subsequent transfers that are necessary to obtain the target weight.

* * * * *